US012631617B2

(12) United States Patent
Heron et al.

(10) Patent No.: US 12,631,617 B2
(45) Date of Patent: May 19, 2026

(54) SENSING INTERACTIONS BETWEEN MOLECULAR ENTITIES AND NANOPORES

(71) Applicant: Oxford Nanopore Technologies plc., Oxford (GB)

(72) Inventors: Andrew John Heron, Oxford (GB); Mark John Bruce, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 1072 days.

(21) Appl. No.: 17/612,605

(22) PCT Filed: May 21, 2020

(86) PCT No.: PCT/GB2020/051237
§ 371 (c)(1),
(2) Date: Nov. 19, 2021

(87) PCT Pub. No.: WO2020/234595
PCT Pub. Date: Nov. 26, 2020

(65) Prior Publication Data
US 2022/0221441 A1        Jul. 14, 2022

(30) Foreign Application Priority Data

May 22, 2019    (GB) ...................................... 1907243

(51) Int. Cl.
*G01N 33/487*        (2006.01)
*G01N 27/327*        (2006.01)

(52) U.S. Cl.
CPC ... *G01N 33/48721* (2013.01); *G01N 27/3272* (2013.01); *G01N 33/48728* (2013.01)

(58) Field of Classification Search
CPC ......... G01N 27/3272; G01N 33/48721; G01N 33/48728; G01N 33/48707
See application file for complete search history.

(56) References Cited

U.S. PATENT DOCUMENTS

| | | | | |
|---|---|---|---|---|
| 8,828,208 B2 * | 9/2014 | Canas | .............. | G01N 33/48728 |
| | | | | 204/600 |
| 2012/0133354 A1 * | 5/2012 | Canas | ................ | G01N 27/3272 |
| | | | | 324/71.1 |

(Continued)

FOREIGN PATENT DOCUMENTS

| | | |
|---|---|---|
| WO | WO 2000/28312 | 5/2000 |
| WO | WO 2000/79257 A1 | 12/2000 |

(Continued)

OTHER PUBLICATIONS

Misawa et al., Membrane protein-based biosensors, 2018, J. R. Soc. Interface, 15, pp. 1-17 (Year: 2018).*

(Continued)

*Primary Examiner* — James Lin
*Assistant Examiner* — Vivian A Tran
(74) *Attorney, Agent, or Firm* — Wolf, Greenfield & Sacks, P.C.

(57)        ABSTRACT

A biochemical sensing system senses interactions between molecular entities and nanopores using a sensor device comprising an array of sensor elements that support the nanopores. A switch arrangement selectively connects detection channels for amplifying sensed electrical signals to respective sensor elements. On the basis of an analysis of the amplified electrical signal output from the detection channels, detection of completion of interactions at sensor elements occurs. In response thereto, the switch arrangement is controlled to connect the detection channel connected to a sensor element at which completion of an interaction has been detected to a further sensor element.

19 Claims, 3 Drawing Sheets

(56) References Cited

U.S. PATENT DOCUMENTS

| | | | |
|---|---|---|---|
| 2014/0221249 A1 | 8/2014 | Chen et al. | |
| 2017/0233804 A1* | 8/2017 | Reid ...................... | G16B 30/00 |
| | | | 435/6.15 |
| 2019/0204294 A1 | 7/2019 | Han et al. | |

FOREIGN PATENT DOCUMENTS

| | | |
|---|---|---|
| WO | WO 2005/124888 A1 | 12/2005 |
| WO | WO 2009/035647 A1 | 3/2009 |
| WO | WO 2009/077734 A2 | 6/2009 |
| WO | WO 2010/055307 A1 | 5/2010 |
| WO | WO 2010/086602 A1 | 8/2010 |
| WO | WO 2010/086603 A1 | 8/2010 |
| WO | WO 2010/109197 A2 | 9/2010 |
| WO | WO 2010/122293 A1 | 10/2010 |
| WO | WO 2011/046706 A1 | 4/2011 |
| WO | WO 2011/067559 A1 | 6/2011 |
| WO | WO 2012/005857 A1 | 1/2012 |
| WO | WO 2012/033524 A2 | 3/2012 |
| WO | WO 2012/107778 A2 | 8/2012 |
| WO | WO 2012/138357 A1 | 10/2012 |
| WO | WO 2012/164270 A1 | 12/2012 |
| WO | WO 2013/153359 A1 | 10/2013 |
| WO | WO 2014/064443 A2 | 5/2014 |
| WO | WO 2014/064444 A1 | 5/2014 |
| WO | WO 2015/140535 A1 | 9/2015 |
| WO | WO 2015/150786 A1 | 10/2015 |
| WO | WO 2016/034591 A2 | 3/2016 |
| WO | WO 2016/059427 A1 | 4/2016 |
| WO | WO 2016/181118 A1 | 11/2016 |
| WO | WO 2016/187519 A1 | 11/2016 |
| WO | WO 2018/100370 A1 | 6/2018 |

OTHER PUBLICATIONS

United Kingdom Search Report for Application No. GB1907243.8 mailed Nov. 13, 2019.

International Search Report and Written Opinion for Application No. PCT/GB2020/051237 mailed Sep. 11, 2020.

International Preliminary Report on Patentability for Application No. PCT/GB2020/051237 mailed Dec. 2, 2021.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

González-Pérez et al., Biomimetic triblock copolymer membrane arrays: a stable template for functional membrane proteins. Langmuir. Sep. 15, 2009;25(18):10447-50. doi: 10.1021/la902417m.

Ivanov et al., DNA tunneling detector embedded in a nanopore. Nano Lett. Jan. 12, 2011;11(1):279-85. doi: 10.1021/nl103873a. Epub Dec. 6, 2010.

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010. Author Manuscript, 21 pages.

Liu et al., Adding new chemistries to the genetic code. Annu Rev Biochem. 2010;79:413-44. doi: 10.1146/annurev.biochem.052308.105824.

Luan et al., Base-by-base ratcheting of single stranded DNA through a solid-state nanopore. Phys Rev Lett. Jun. 11, 2010;104(23):238103. doi: 10.1103/PhysRevLett.104.238103. Epub Jun. 10, 2010. Author Manuscript, 9 pages.

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Multiple base-recognition sites in a biological nanopore: two heads are better than one. Angew Chem Int Ed Engl. 2010;49(3):556-9. doi: 10.1002/anie.200905483. Author Manuscript, 8 pages.

Stoddart et al., Nucleobase recognition in ssDNA at the central constriction of the alpha-hemolysin pore. Nano Lett. Sep. 8, 2010;10(9):3633-7. doi: 10.1021/nl101955a. Author Manuscript, 11 pages.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

* cited by examiner

SENSING INTERACTIONS BETWEEN MOLECULAR ENTITIES AND NANOPORES

RELATED APPLICATIONS

This application is a national stage filing under 35 U.S.C. § 371 of international application number PCT/GB2020/051237, filed May 21, 2020, which claims the benefit of the filing date of Great Britain application number GB 1907243.8, filed May 22, 2019, the entire contents of each of which are incorporated herein by reference.

FIELD

The present invention relates to the sensing of interactions between molecular entities and nanopores.

BACKGROUND

The use of nanopores to sense interactions with molecular entities, for example polynucleotides is a powerful technique that has been subject to much recent development. Sensor devices have been developed that comprise array of sensor elements arranged to support respective nanopores, thereby increasing data collection by allowing plural nanopores to sense interactions in parallel, typically from the same sample. The present invention is concerned with further improving throughput and sensitivity.

According to a first aspect of the present invention, there is provided a method of sensing interactions between molecular entities and nanopores, the method comprising: providing a sensor device comprising an array of sensor elements arranged to support respective nanopores that are capable of an interaction with a molecular entity and including respective electrodes, each sensor element being arranged to output an electrical signal at the electrode that is dependent on an interaction of a molecular entity with the nanopore; providing a detection circuit comprising: a plurality of detection channels each capable of amplifying an electrical signal from one of the sensor elements, the number of sensor elements in the array being greater than the number of detection channels; and a switch arrangement capable of selectively connect the detection channels to respective sensor elements; controlling the switch arrangement to connect detection channels to respective sensor elements; and detecting, on the basis of an analysis of the amplified electrical signal output from the detection channels, completion of interactions at sensor elements, and in response thereto, controlling the switch arrangement to connect the respective detection channel that is connected to a sensor element at which completion of an interaction has been detected to a further sensor element that is not currently connected to a detection channel.

The present invention therefore applies a detection circuit with plural detection channels that allow parallel sensing of electrical signals from sensor elements of an array. There are a greater number of sensor elements than detection channels and a switching circuit is used to connect detection channels to respective sensor elements, thereby providing a multiplexed system.

A configuration of an array of sensor elements, plural detection channels and a switching arrangement is known in itself from WO-2010/122293 which teaches selecting sensor elements in which a membrane is formed and an acceptable number of membrane proteins have inserted, for the purpose of increasing the utilisation of detection channels when the formation of membranes and the insertion of membrane proteins is subject to random processes resulting in incomplete preparation of sensor elements of acceptable quality. However, in the present invention the switch arrangement is controlled in a different manner for a different purpose.

Specifically, in the present invention, detection of completion of interactions at sensor elements is detected on the basis of an analysis of the amplified electrical signal output from the detection channels, and, in response thereto, the switch arrangement is controlled to connect a respective detection channel that is connected to a sensor element at which completion of an interaction has been detected to a further sensor element that is not currently connected to a detection channel, thereby allowing the detection of an electrical signal from the further sensor element. In practice, the average waiting time between successive interactions can be significantly reduced, enabling higher throughput even under saturating concentrations of the molecular entities.

Similarly, sensitivity is increased, because a smaller amount of sample is required to saturate the sensing time. The amount of sample supplied to the sensing device can be reduced without significantly impacting the sensing throughput, especially in the regime where the average time between interactions is less than the average interaction period. Surprisingly, this has been found to increase the overall throughput of sensing of a molecular entities in a sample that is supplied to the array of sensor elements in the sensor device. This benefit is achieved as follows. On completion of interaction at any given sensor element, there is a delay waiting for another molecular entity to become available. However, it has been appreciated that the probability of a molecular entity being available at another sensor element is greater, such that the delay until another interaction is likely to be reduced. The availability of molecular entities to the sensor elements is typically subject to random processes so the delay is reduced on average even if it cannot be guaranteed that the delay will be reduced on every instance of switching.

The overall reduction in the delay may be improved by applying the present invention to a sensor element in which means are provided for capturing molecular entities in the vicinity of the nanopore. This further increases the overall throughput by further increasing the probability of a molecular entity being available at a further sensor element because it has been captured during the period of interaction at the sensor element previously connected to the detection channel.

Such capture may be achieved, for example by the sensor elements and/or molecular entities being adapted to capture molecular entities within a vicinity of the respective nanopore. Similarly, such capture may be achieved by the sensor elements further comprising capture moieties arranged to capture molecular entities within a vicinity of the respective nanopores. Various examples of such capture moieties are known. For example, the capture moieties may be tethers which bind to the molecular entities and which may be attached to the nanopore or to a membrane in a case where which the nanopore is inserted therein.

Such capture may be achieved by other means, for example by application of a suitable bias signal to the electrodes of the sensor elements.

This effect may be enhanced by determining, on the basis of an analysis of the amplified electrical signal output from the respective detection channel, whether a molecular entity is available for interaction at the further sensor element, and in response to determining that a molecular entity is available for interaction continuing to connect the respective detection channel to the further sensor element, or in response to determining that a molecular entity is not available for interaction controlling the switch arrangement to connect the respective detection channel to a yet further sensor element that is not currently connected to a detection channel. In this manner, plural further sensor elements may be tested, thereby increasing the overall probability of finding an molecular entity available for interaction, and correspondingly increasing the throughput.

The present invention provides particular benefits in the case that the molecular entities are polymers, such as polynucleotides, and the sensor elements are arranged to support respective nanopores that are capable of interacting with the molecular entities during translocation of the molecular entities with respect to the nanopore, for example through the nanopore. In this case the improvement in throughput is particularly high because of the relatively long interaction period. Thus, improvements are achieved for molecular entities such as long fragment libraries of polynucleotides. For example, libraries with fragment sizes of order 100 kb ("kb" standing for kilobase) can takes from tens of seconds up to minutes between interactions when relying on diffusion for delivery to the nanopores. However, such large fragments also take a long time to interact (for example 100 kb at 500 bases per second takes 200 seconds), and this time is effectively used to make the next fragment available on another unused sensor element.

According to a second aspect of the present invention, there is provided a biochemical sensing system for sensing interactions between molecular entities and nanopores, the biochemical sensing system comprising: a sensor device comprising an array of sensor elements arranged to support respective nanopores that are capable of an interaction with a molecular entity and including respective electrodes, each sensor element being arranged to output an electrical signal at the electrode that is dependent on an interaction of a molecular entity with the nanopore; and a detection circuit comprising: a plurality of detection channels each capable of amplifying an electrical signal from one of the sensor elements, the number of sensor elements in the array being greater than the number of detection channels; a switch arrangement capable of selectively connect the detection channels to respective sensor elements; and a controller arranged to control the switching of the switch arrangement to connect detection channels to respective sensor elements, wherein the controller is arranged to detect, on the basis of an analysis of the amplified electrical signal output from the detection channels, completion of interactions at sensor elements, and in response thereto, to control the switch arrangement to connect the respective detection channel that is connected to a sensor element at which completion of an interaction has been detected to a further sensor element that is not currently connected to a detection channel.

BRIEF DESCRIPTION OF THE FIGURES

To allow better understanding, embodiments of the present invention will now be described by way of non-limitative example with reference to the accompanying drawings, in which.

DETAILED DESCRIPTION

Figure 1:
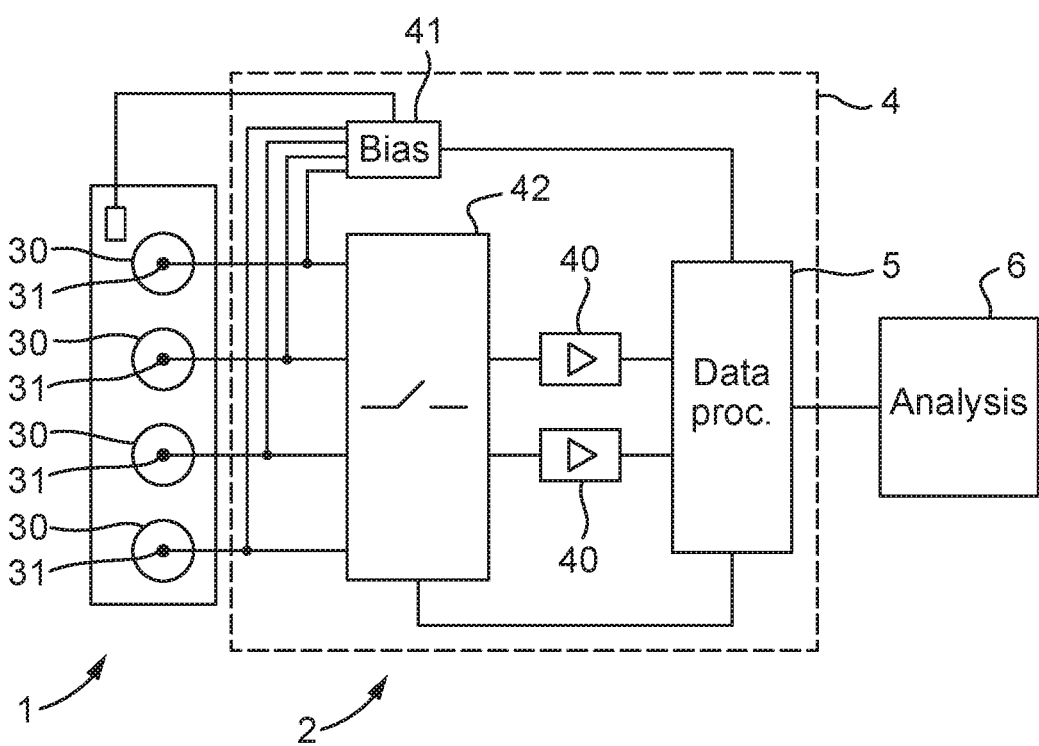
FIG. 1 is diagram of a biochemical sensing system.

A biochemical sensing system 1 for sensing interactions of a molecular entities with nanopores is shown in FIG. 1. The biochemical sensing system 1 comprises a sensing apparatus 2 comprising a sensor device 3 and a detection circuit 4 that is connected to the sensor device 3.

The sensor device 3 comprises an array of sensor elements 30 that each support respective nanopores that are capable of an interaction with a molecular entity. The sensor elements 30 comprise respective electrodes 31. In use, each sensor elements 30 outputs an electrical signal at its electrode 31 that is dependent on an interaction of a molecular entity with the nanopore. The sensor device 3 is illustrated schematically in FIG. 1 but may have a variety of configurations, some non-limitative examples being as follows.

Figure 2:
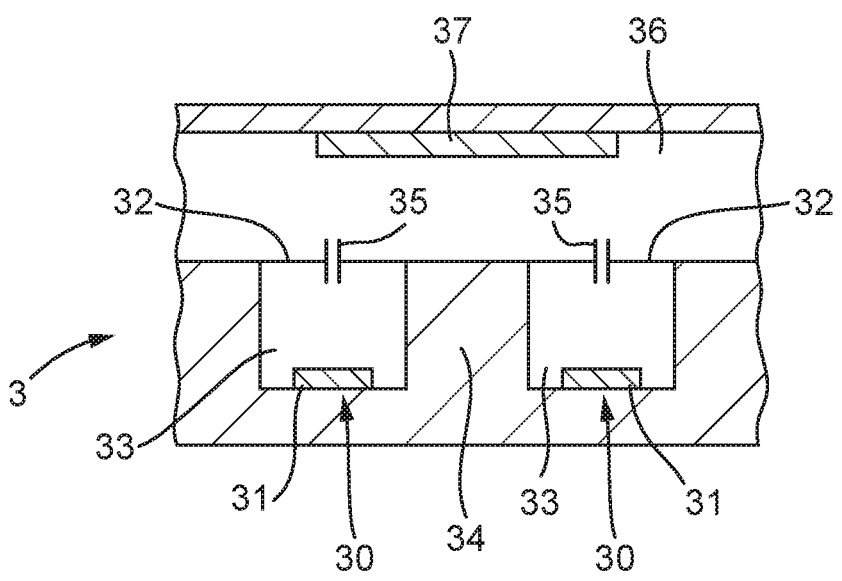
FIG. 2 is a schematic cross-sectional view of a sensor device.

In one example, the sensor device 3 may have the form shown in FIG. 2. Herein, the sensor device 2 comprises an array of sensor elements 30 which each comprise a membrane 32 supported across a well 33 in a substrate 34 with a nanopore 35 inserted in the membrane 32. The membrane 31 may be made of amphiphilic molecules such as lipid as discussed further below. Each membrane 32 seals the respective well 33 from a sample chamber 36 which extends across the array of sensor elements 30 and is in fluid communication with each nanopore 35. Each well 33 has a sensor electrode 32 arranged therein. A common electrode 37 is provided in the sample chamber 36 for providing a common reference potential to each sensor element 30. In use, the sample chamber 36 receives a sample containing molecular entities which interact with the nanopores 35 of the sensor elements 30.

Two sensor elements 30 are shown in FIG. 2 for clarity, but in general any number of sensor elements 30 may be provided. Typically, a large number of sensor elements 30 may be provided to optimise the data collection rate, for example 256, 1024, 4096 or more sensor elements 30.

The sensor device 3 may have a detailed construction as disclosed in WO-2009/077734 or WO-2014/064443

The nanopore and associated elements of the sensor elements 30 may be as follows, without limitation to the example shown in FIG. 2.

The nanopore is a pore, typically having a size of the order of nanometres. In embodiments where the molecular entities are polymers that interact with the nanopore while translocating therethrough in which case the nanopore is of a suitable size to allow the passage of polymers therethrough.

The nanopore may be a protein pore or a solid state pore. The dimensions of the pore may be such that only one polymer may translocate the pore at a time.

Where the nanopore is a protein pore, it may have the following properties.

The nanopore may be a transmembrane protein pore. Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, lysenin, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL). The transmembrane pore may be derived from lysenin. Suitable pores derived from lysenin are disclosed in WO 2013/153359. Suitable pores derived from MspA are disclosed in WO-2012/107778. The pore may be derived from CsgG, such as disclosed in WO-2016/034591. The pore may be a DNA origami pore.

The protein pore may be a naturally occurring pore or may be a mutant pore. Typical pores are described in WO-2010/109197, Stoddart D et al., Proc Natl Acad Sci, 12; 106(19): 7702-7, Stoddart D et al., Angew Chem Int Ed Engl. 2010; 49(3):556-9, Stoddart D et al., Nano Lett. 2010 September 8; 10(9):3633-7, Butler T Z et al., Proc Natl Acad Sci 2008; 105(52):20647-52, and WO-2012/107778.

The protein pore may be one of the types of protein pore described in WO-2015/140535 and may have the sequences that are disclosed therein.

Where the nanopore is a protein pore, it may be inserted into a membrane that is supported in the sensor element 30. Such a membrane may be an amphiphilic layer, for example a lipid bilayer. An amphiphilic layer is a layer formed from amphiphilic molecules, such as phospholipids, which have both hydrophilic and lipophilic properties. The amphiphilic layer may be a monolayer or a bilayer. The amphiphilic layer may be a co-block polymer such as disclosed in Gonzalez-Perez et al., Langmuir, 2009, 25, 10447-10450 or WO-2014/064444. Alternatively, a protein pore may be inserted into an aperture provided in a solid state layer, for example as disclosed in WO-2012/005857.

The nanopore may comprise an aperture formed in a solid state layer, which may be referred to as a solid state pore. The aperture may be a well, gap, channel, trench or slit provided in the solid state layer along or into which analyte may pass. Such a solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in WO-2009/035647, WO-2011/046706 or WO-2012/138357. Suitable methods to prepare an array of solid state pores is disclosed in WO-2016/187519.

Such a solid state pore is typically an aperture in a solid state layer. The aperture may be modified, chemically, or otherwise, to enhance its properties as a nanopore. A solid state pore may be used in combination with additional components which provide an alternative or additional measurement of the polymer such as tunneling electrodes (Ivanov A P et al., Nano Lett. 2011 Jan. 12; 11(1):279-85), or a field effect transistor (FET) device (as disclosed for example in WO-2005/124888). Solid state pores may be formed by known processes including for example those described in WO-00/79257

Molecular entities interact with the nanopores in the sensor elements 30 causing output an electrical signal at the electrode 31 that is dependent on that interaction. In one type of sensor device 3, the electrical signal may be the ion current flowing through the nanopore. Similarly, electrical properties other than ion current may be measured. Some examples of alternative types of property include without limitation: ionic current, impedance, a tunneling property, for example tunneling current (for example as disclosed in Ivanov A P et al., Nano Lett. 2011 Jan. 12; 11(1):279-85), and a FET (field effect transistor) voltage (for example as disclosed in WO2005/124888). One or more optical properties may be used, optionally combined with electrical properties (Soni G V et al., Rev Sci Instrum. 2010 January; 81(1):014301). The property may be a transmembrane current, such as ion current flow through a nanopore. The ion current may typically be the DC ion current, although in principle an alternative is to use the AC current flow (i.e. the magnitude of the AC current flowing under application of an AC voltage).

The interaction may occur during translocation of the molecular entities with respect to the nanopore, for example through the nanopore.

The electrical signal provides as series of measurements of a property that is associated with an interaction between the molecular entity and the nanopore. Such an interaction may occur at a constricted region of the nanopore. For example in the case that the molecular entity is a polymer comprising a series of polymer units which translocate with respect to the nanopore, the measurements may be of a property that depends on the successive polymer units translocating with respect to the pore.

Ionic solutions may be provided on either side of the nanopore. A sample containing the molecular entities of interest that are polymers may be added to one side of the nanopore, for example in the sample chamber 36 in the sensor device of FIG. 2. membrane and allowed to translocate with respect to the nanopore, for example under a potential difference or chemical gradient. The electrical signal may be derived during the translocation of the polymer with respect to the pore, for example taken during translocation of the polymer through the nanopore. The polymer may partially translocate with respect to the nanopore.

In order to allow measurements to be taken as a polymer translocates through a nanopore, the rate of translocation can be controlled by a binding moiety that binds to the polymer. Typically the binding moiety can move a polymer through the nanopore with or against an applied field. The binding moiety can be a molecular motor using for example, in the case where the binding moiety is an enzyme, enzymatic activity, or as a molecular brake. Where the polymer is a polynucleotide there are a number of methods proposed for controlling the rate of translocation including use of polynucleotide binding enzymes. Suitable enzymes for controlling the rate of translocation of polynucleotides include, but are not limited to, polymerases, helicases, exonucleases, single stranded and double stranded binding proteins, and topoisomerases, such as gyrases. For other polymer types, binding moieties that interact with that polymer type can be used. The binding moiety may be any disclosed in WO-2010/086603, WO-2012/107778, and Lieberman K R et al, J Am Chem Soc. 2010; 132(50):17961-72), and for voltage gated schemes (Luan B et al., Phys Rev Lett. 2010; 104(23):238103).

The binding moiety can be used in a number of ways to control the polymer motion. The binding moiety can move the polymer through the nanopore with or against the applied field. The binding moiety can be used as a molecular motor using for example, in the case where the binding moiety is an enzyme, enzymatic activity, or as a molecular brake. The translocation of the polymer may be controlled by a molecular ratchet that controls the movement of the polymer through the pore. The molecular ratchet may be a polymer binding protein. For polynucleotides, the polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target polynucleotide and controlling its movement through the pore. For instance, the enzyme may be modified to remove its enzymatic activity or may be used under conditions which prevent it from acting as an enzyme. Such conditions are discussed in more detail below.

Preferred polynucleotide handling enzymes are polymerases, exonucleases, helicases and topoisomerases, such as gyrases. The polynucleotide handling enzyme may be for example one of the types of polynucleotide handling enzyme described in WO-2015/140535 or WO-2010/086603.

Translocation of the polymer through the nanopore may occur, either cis to trans or trans to cis, either with or against an applied potential. The translocation may occur under an applied potential which may control the translocation.

Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential. Alternatively, the single strand DNA dependent polymerases can act as a molecular brake slowing down the movement of a polynucleotide through the pore. Any moieties, techniques or enzymes described in WO-2012/107778 or WO-2012/033524 could be used to control polymer motion.

The sensor elements 30 and/or the molecular entities may be adapted to capture capture molecular entities within a vicinity of the respective nanopores. For example sensor elements 30 may further comprise capture moieties arranged to capture molecular entities within a vicinity of the respective nanopores. The capture moieties may be any of the binding moieties or exonucleases described above with also have the purpose of controlling the translocation, or may be separately provided.

The capture moieties may be attached to the nanopores of the sensor elements. At least one capture moiety may be attached to the nanopore of each sensor element.

The capture moiety may be a tag or tether which binds to the molecular entities. In that case the molecular entity may be adapted to achieve that binding.

Such a tag or tether may be attached to the nanopore, for example as disclosed in WO-2018/100370, and as further described herein below.

Alternatively in a case the nanopore is inserted in a membrane, such a tag or tether may be attached to the membrane, for example as disclosed in WO-2012/164270.

The methods described herein may comprise the use of adapters which adapt the molecular entities for the purpose of capturing them. By way of example, polynucleotide adapters suitable for use in nanopore sequencing of polynucleotides are known in the art. Adapters for use in nanopore sequencing of polynucleotides may comprise at least one single stranded polynucleotide or non-polynucleotide region. For example, Y-adapters for use in nanopore sequencing are known in the art. A Y adapter typically comprises (a) a double stranded region and (b) a single stranded region or a region that is not complementary at the other end. A Y adapter may be described as having an overhang if it comprises a single stranded region. The presence of a non-complementary region in the Y adapter gives the adapter its Y shape since the two strands typically do not hybridise to each other unlike the double stranded portion. The Y adapter may comprise one or more anchors.

The Y adapter preferably comprises a leader sequence which preferentially threads into the pore. The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The single stranded leader sequence most preferably comprises a single strand of DNA, such as a poly dT section. The leader sequence preferably comprises the one or more spacers. The leader sequence can be any length, but is typically 10 to 150 nucleotides in length, such as from 20 to 150 nucleotides in length. The length of the leader typically depends on the membrane-embedded nanopore used in the method. The leader sequence preferentially threads into the transmembrane pore and thereby facilitates the movement of polynucleotide through the pore. The adapter may be ligated to a DNA molecule using any method known in the art.

A polynucleotide adapter may comprise a membrane anchor or a transmembrane pore anchor attached to the adapter. For example, a membrane anchor or transmembrane pore anchor may promote localisation of the adapter and coupled polynucleotide within a vicinity of the nanopore. The anchor may be a polypeptide anchor and/or a hydrophobic anchor that can be inserted into the membrane. In one embodiment, the hydrophobic anchor is a lipid, fatty acid, sterol, carbon nanotube, polypeptide, protein or amino acid, for example cholesterol, palmitate or tocopherol. The anchor may comprise thiol, biotin or a surfactant. The anchor may be biotin (for binding to streptavidin), amylose (for binding to maltose binding protein or a fusion protein), Ni-NTA (for binding to poly-histidine or poly-histidine tagged proteins) or peptides (such as an antigen).

The anchor may comprise a linker, or 2, 3, 4 or more linkers. Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The adapter may hybridise to a complementary sequence on a circular polynucleotide linker. The one or more anchors or one or more linkers may comprise a component that can be cut or broken down, such as a restriction site or a photolabile group. The linker may be functionalised with maleimide groups to attach to cysteine residues in proteins. Suitable linkers are described in WO 2010/086602. The anchor may be cholesterol or a fatty acyl chain. For example, any fatty acyl chain having a length of from 6 to 30 carbon atom, such as hexadecanoic acid, may be used. Examples of suitable anchors and methods of attaching anchors to adapters are disclosed in WO 2012/164270 and WO 2015/150786.

Examples of tags and tethers which are attached to the nanopore are as follows.

Nanopores for use in the methods described herein may be modified to comprise one or more binding sites for binding to one or more analytes (e.g. molecular entities) and thereby acting as a capture moeity. In some embodiments, the nanopores may be modified to comprise one or more binding sites for binding to an adaptor attached to the analytes. For example, in some embodiments, the nanopores may bind to a leader sequence of the adaptor attached to the analytes. In some embodiments, the nanopores may bind to a single stranded sequence in the adaptor attached to the analytes.

In some embodiments, the nanopores are modified to comprise one or more tags or tethers, each tag or tether comprising a binding site for the analyte. In some embodiments, the nanopores are modified to comprise one tag or tether per nanopore, each tag or tether comprising a binding site for the analyte.

A short oligonucleotide attached to the transmembrane pore, which oligonucleotide comprises a sequence complementary to a sequence in the leader sequence or another single stranded sequence in the adaptor may be used to enhance capture of the target polynucleotide.

In some embodiments, the tag or tether may comprise or be an oligonucleotide (e.g., DNA, RNA, LNA, BNA, PNA, or morpholino). The oligonucleotide (e.g., DNA, RNA, LNA, BNA, PNA, or morpholino) can have about 10-30 nucleotides in length or about 10-20 nucleotides in length.

In some embodiments, the oligonucleotide (e.g., DNA, RNA, LNA, BNA, PNA, or morpholino) for use in the tag or tether can have at least one end (e.g., 3'- or 5'-end) modified for conjugation to other modifications or to a solid substrate surface including, e.g., a bead. The end modifiers may add a reactive functional group which can be used for conjugation. Examples of functional groups that can be added include, but are not limited to amino, carboxyl, thiol, maleimide, aminooxy, and any combinations thereof. The functional groups can be combined with different length of spacers (e.g., C3, C9, C12, Spacer 9 and 18) to add physical distance of the functional group from the end of the oligonucleotide sequence.

In some embodiments, the tag or tether may comprise or be a morpholino oligonucleotide. The morpholino oligonucleotide can have about 10-30 nucleotides in length or about 10-20 nucleotides in length. The morpholino oligonucleotides can be modified or unmodified. For example, in some embodiments, the morpholino oligonucleotide can be modified on the 3' and/or 5' ends of the oligonucleotides. Examples of modifications on the 3' and/or 5' end of the morpholino oligonucleotides include, but are not limited to 3' affinity tag and functional groups for chemical linkage (including, e.g., 3'-biotin, 3'-primary amine, 3'-disulfide amide, 3'-pyridyl dithio, and any combinations thereof); 5' end modifications (including, e.g., 5'-primary amine, and/or 5'-dabcyl), modifications for click chemistry (including, e.g., 3'-azide, 3'-alkyne, 5'-azide, 5'-alkyne), and any combinations thereof.

In some embodiments, the tag or tether may further comprise a polymeric linker, e.g., to facilitate coupling to a nanopore. An exemplary polymeric linker includes, but is not limited to polyethylene glycol (PEG). The polymeric linker may have a molecular weight of about 500 Da to about 10 kDa (inclusive), or about 1 kDa to about 5 kDa (inclusive). The polymeric linker (e.g., PEG) can be functionalized with different functional groups including, e.g., but not limited to maleimide, NHS ester, dibenzocyclooctyne (DBCO), azide, biotin, amine, alkyne, aldehyde, and any combinations thereof. In some embodiments, the tag or tether may further comprise a 1 kDa PEG with a 5'-maleimide group and a 3'-DBCO group. In some embodiments, the tag or tether may further comprise a 2 kDa PEG with a 5'-maleimide group and a 3'-DBCO group. In some embodiments, the tag or tether may further comprise a 3 kDa PEG with a 5'-maleimide group and a 3'-DBCO group. In some embodiments, the tag or tether may further comprise a 5 kDa PEG with a 5'-maleimide group and a 3'-DBCO group.

Other examples of a tag or tether include, but are not limited to His tags, biotin or streptavidin, antibodies that bind to analytes, aptamers that bind to analytes, analyte binding domains such as DNA binding domains (including, e.g., peptide zippers such as leucine zippers, single-stranded DNA binding proteins (SSB)), and any combinations thereof.

The tag or tether may be attached to the external surface of the nanopore, e.g., on the cis side of a membrane, using any methods known in the art. For example, one or more tags or tethers can be attached to the nanopore via one or more cysteines (cysteine linkage), one or more primary amines such as lysines, one or more non-natural amino acids, one or more histidines (His tags), one or more biotin or streptavidin, one or more antibody-based tags, one or more enzyme modification of an epitope (including, e.g., acetyl transferase), and any combinations thereof. Suitable methods for carrying out such modifications are well-known in the art. Suitable non-natural amino acids include, but are not limited to, 4-azido-L-phenylalanine (Faz) and any one of the amino acids numbered 1-71 in FIG. 1 of Liu C. C. and Schultz P. G., Annu. Rev. Biochem., 2010, 79, 413-444.

In some embodiments where one or more tags or tethers are attached to the nanopore via cysteine linkage(s), the one or more cysteines can be introduced to one or more monomers that form the nanopore by substitution.

In some embodiments, the tag or tether may be attached directly to the nanopore or via one or more linkers. The tag or tether may be attached to the nanopore using the hybridization linkers described in WO 2010/086602. Alternatively, peptide linkers may be used. Peptide linkers are amino acid sequences. The length, flexibility and hydrophilicity of the peptide linker are typically designed such that it does not to disturb the functions of the monomer and pore. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$ and $(SG)_8$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

The transmembrane pore may be modified to enhance capture of polynucleotides. For example, the pore may be modified to increase the positive charges within the entrance to the pore and/or within the barrel of the pore. Such modifications are known in the art. For example, WO 2010/055307 discloses mutations in α-hemolysin that increase positive charge within the barrel of the pore.

Modified MspA, lysenin and CsgG pores comprising mutations that enhance polynucleotide capture are disclosed in WO 2012/107778, WO 2013/153359 and WO 2016/034591, respectively. Any of the modified pores disclosed in these publications may be used herein.

The arrangement of the detection circuit 4 will now be discussed. The detection circuit 4 is connected to the electrodes 31 of each sensor element 30 and has the primary function of process the electrical signals output therefrom. The detection circuit 4 also has the function of controlling the application of bias signals to each sensor element 30.

The detection circuit 4 includes plural detection channels 40. Each detection channel 40 receives an electrical signal from a single sensor electrode 31 and is arranged to amplify that electrical signal. The detection channel 40 is therefore designed to amplify very small currents with sufficient resolution to detect the characteristic changes caused by the interaction of interest. The detection channel 40 is also designed with a sufficiently high bandwidth to provide the time resolution needed to detect each such interaction. These constraints require sensitive and therefore expensive components. Each detection channel 40 may be similar to standard single channel recording equipment as describe in Stoddart D et al., Proc Natl Acad Sci, 12; 106(19):7702-7, Lieberman K R et al, J Am Chem Soc. 2010; 132(50):17961-72, and WO-2000/28312. Alternatively, each detection channel 40 may be arranged as described in detail in WO-2010/122293, WO-2011/067559 or WO-2016/181118.

The number of sensor elements 30 in the array is greater than the number of detection channels 40 and the biochemical sensing system is operable to take measurements of a polymer from sensor elements 30 selected in an multiplexed manner, in particular an electrically multiplexed manner. This is achieved by providing a switch arrangement 42 between the sensor electrodes 31 of the sensor elements 30 and the detection channels 40. For clarity, FIG. 6 shows a simplified example with four sensor elements 30 and two detection channels 40, but the number of sensor cells 30 and detection channels 40 is typically much greater. For example, for some applications, the sensor device 2 might comprise a total of 4096 sensor elements 30 and 1024 detection channels 40.

The switch arrangement 42 may be arranged as described in detail in WO-2010/122293. For example, the switch arrangement 42 may comprise plural 1-to-N multiplexers each connected from a detection channel 40 to a group of N sensor elements 30 and may include appropriate hardware such as a latch to select the state of the switching.

By switching of the switch arrangement 42, the biochemical sensing system 1 may be operated to amplify electrical signals from sensor elements 30 selected in an electrically multiplexed manner. The detection circuit 4 includes a data processor 5 which receives the output signals from the detection channels 40. The data processor 5 acts as a controller that controls the switch arrangement 42 to connect detection channels 40 to respective sensor elements 30 as described further below.

In addition, the detection circuit 4 includes a bias control circuit 41 to perform the function of controlling the application of bias signals to each sensor element 30. The bias control circuit 41 is connected to the common electrode 37 and to the sensor electrodes 31 of each sensor device 30. The bias signals are selected to bias the sensor electrodes 31 with respect to common electrode 37 to control translocation of the molecular entities with respect to the nanopores. In general, it would be possible for a bias signal supplied to a given sensor element 30 to be a drive bias signal that causes translocation to occur at the sensor element 30 or an inhibition bias signal that inhibits translocation to occur at the sensor element 30.

The bias control circuit 41 is controlled by the data processor 5. The data processor may select two modes of operation for the bias control circuit 41.

In the first mode of operation of the bias control circuit 41, drive bias signals are supplied to all the sensor elements 30, thereby causing translocation of the molecular entities with respect to the nanopores of each sensor elements 30 where a molecular entity is available. In this first mode of operation, translocation may be occurring at any sensor element 30 irrespective of whether an electrical signal from the sensor element 30 is being supplied to a detection channel 40 by the switch arrangement 42. The occurrence of translocation is therefore dependent only on the random processes by which molecular entities are made available to the sensor elements 30. In the case that the sensor elements 30 comprise capture moieties as described above, then translocation occurs subsequent to capture but without any electrical signal being supplied to a detection channel.

In the second mode of operation of the bias control circuit 41, the bias control circuit 41 is controlled synchronously with the switching of the switch arrangement 42 so as to supply drive bias signals to respective sensor elements 30 when they are connected to a detection channel 41 and to supply inhibition bias signals to respective sensor elements 30 when they are not connected to a detection channel 40. In this second mode of operation, translocation only occurs at sensor elements 30 when they are connected to a detection channel 41 for supply of an electrical signal. However, translocation is inhibited at sensor elements 30 that are not connected to a detection channel 40 through the switch arrangement. However, at such sensor elements 30 capture of a molecular entity in the vicinity of the sensor element 30 may still occur. For example, such capture may occur by means of the sensor elements 30 comprising capture moieties as described above, or by means of the inhibition bias signal being selected appropriately.

The data processor 5 is arranged as follows. The data processor 5 is connected to the output of the detection channels 40 and is supplied with the amplified electrical signals therefrom. The data processor 5 stores and analyses the amplified electrical signals and on the basis of that analysis controls the other elements of the detection circuit, including control of the bias voltage circuit 41 as described above and control of the switch arrangement 42 as described below. The data processor 5 forms part of the detection circuit 2 and may be provided in a common package therewith, possibly on a common circuit board. The data processor 5 may be implemented in any suitable form, for example as a processor running an appropriate computer program or as an ASIC (application specific integrated circuit).

The data processor 5 of the biochemical sensing system 1 is connected to an analysis system 6. The data processor 5 also supplies the amplified output signals to the analysis system 6. The analysis system 6 performs further analysis of the amplified electrical signal which is a raw signal representing measurements of the property measured at the nanopore. Such an analysis system 6 may for example estimate the identity of the molecular entity in its entirety or in the case that the molecular entity is a polymer may estimate the identity of the polymer units thereof. Thus, the analysis system may be configured as a computer apparatus running an appropriate program. Such a computer apparatus may be connected to the data processor 5 of the biochemical sensing system 1 directly or via a network, for example within a cloud-based system.

The method of controlling the detection circuit 2 that is performed by the data processor 5 is shown FIG. 3 and performed as follows. The same method is performed in parallel for each detection channel 40.

The method starts as step S1, at which point none of the sensor elements 30 are connected to a detection channel 40. In the second mode of operation of the bias control circuit 41, at this time inhibition bias signals are supplied to each sensor element 30.

In step S2, the data processor 5 selects which sensor elements 30 is to be connected to each respective detection channel 40. In the first instance of performing step S2, as no information is known about the sensor elements 30, any sensor elements 30 may be selected, for example selecting sensor elements 30 that are evenly spread around the array of sensor elements. In the second mode of operation of the bias control circuit 41, as mentioned above, at the same time the data processor 5 controls the bias control circuit 41 to supply a drive bias signal to the selected sensor elements 30 in place of the inhibition bias signal that was previously supplied.

In step S3, the data processor 5 controls the switch arrangement to connect the sensor elements 30 selected in step S2 to the respective detection channels 40.

In step S4, the amplified electrical signal from the selected sensor elements 30 is received and stored by the data processer for a period of time corresponding to a plurality of measurements. The stored electrical signal provides a "chunk" of data representing the amplified electrical signal over that period of time.

In step S5, the data processor 5 analyses the chunk of data for each respective sensor element 30 and on the basis of that analysis decides whether to continue receiving data from that respective sensor element 30.

In general, when step S5 is performed, at each respective sensor element 30 it is possible that a molecular entity is or is not available for interaction with the nanopore of that sensor element. A molecular entity may be available for interaction because it has been captured in the vicinity of the nanopore using the means described above, for example capture by a capture moiety or by an appropriate bias signal. This may includes cases where the molecular entity has not yet started translocating, or cases where translocation has only just started. Alternatively, a molecular entity may be available for interaction because it has already partially translocated.

In the first mode of operation of the bias control circuit 41, when step S5 is first performed after connection of the selected sensor elements 30 to a respective detection channel 40, translocation may previously have been occurring at any sensor element 30, and so a molecular entity may already be partially translocated through the selected sensor elements 30. Thus, whether or not this is the case at any given sensor element 30 varies due to the random processes that drive capture and translocation in the sensor device 3.

In the second mode of operation of the bias control circuit 41, when step S5 is first performed after connection of the selected sensor elements 30 to a respective detection channel 40, translocation has not previously been occurring at any sensor element 30 due to the supply of the inhibition bias signal, but, and so a molecular entity may already be partially translocated through the selected sensor elements

30 but a molecular entity may be available for interaction because it has been captured in the vicinity of the nanopore using the means described above. Again, whether or not this is the case at any given sensor element 30 varies due to the random processes that drive capture of molecular entities in the sensor device 3.

The analysis performed in step S5 involves determination of whether the amplified electrical signal represents that a molecular entity is available for interaction with the nanopore of the respective sensor element 30. This determination is possible because the electrical signal is characteristic of whether or not a molecular entity is available for interaction. For example, in the case of that the measured property is ion current flowing through the nanopore, the ion current may have a relatively high level when no molecular entity is available for interaction and a relatively low level when a molecular entity is available for interaction due to the molecular entity blocking the pore. Thus, it is straightforward to determine whether or not a molecular entity is available for interaction for example by low pass-filtering the amplified electrical signal and testing it against thresholds that distinguish the different situations. In the case of other measured properties, similar characteristics may be used to make determinations in step S5.

Thus, in step S5, the data processor 5 determines on the basis of an analysis of the chunk of data if a molecular entity is available for interaction with the nanopore of the sensor element 30 that has been selected. If so, then the step S5 results in a decision to continue receiving data from that respective sensor element 30 and the method reverts to step S4. Otherwise, step S5 results in a decision to not to continue receiving data from that respective sensor element 30 and so the method reverts to step S2.

Considering the first time that step S5 is performed after controlling the switch arrangement 42 to connect the detection channel 40 to a new sensor element 30 when there is no molecular entity available for interaction at the new sensor element, this results in step S2 being performed again to select a further new sensor element.

This process is then repeated with one or more new sensor elements 30 selected in successive performance of step S2 until it is detected in step S5 that the detection channel is connected to a sensor element at which a molecular entity is available.

When a molecular entity is available for interaction at the new sensor element 30, then reverting to step S4 causes steps S4 and S5 to be repeated for a further chunk of data corresponding to the electrical signal. Repeated performance of steps S4 and S5 effectively provides recordal of the electrical signal during the period of interaction of a molecular entity until it is determined in step S4 that it is no longer the case that the molecular entity is available for interaction with the nanopore of the sensor element 30. This is effectively a detection of completion of the interaction, and results in the method reverting to step S2 to select a further new sensor element 30.

The overall effect is that whenever completion of interactions at sensor elements 30 is detected, switching of the detection channel to a new sensor element is performed.

In step S2, the data processor 5 may select new sensor elements 30 for connection to the respective detection channels 4 in any suitable manner, taking account of the connections that the switch arrangement 42 is capable of making. For example in the case that the switch arrangement 42 comprises plural 1-to-N multiplexers, the data processor 5 may select sensor elements 30 of each group of N sensor elements 30 successively in a regular cycle for connection to the corresponding detection channel 40. In more complicated approaches, the selection may take account of other information available to the data processor 5. In one example, the data processor 5 may record the interval since the last known interaction at each sensor element 30 and preferentially select sensor elements 30 where having long intervals. In another example, the data processor 5 may record status information about the sensor elements 50 and take that into account in the selection.

In an optional variation, the data processor 5 may additionally analyse the amplified electrical signals to detect sensor elements 30 which do not have an acceptable quality of performance because it is not that case that a membrane has formed and an acceptable number of membrane proteins have inserted, and record the results. In that case, the data processor 5 may avoid selecting sensor elements 30 where this is the case, thereby effectively apply techniques similar to those disclosed in WO-2010/122293 but in combination with the additional steps disclosed herein.

Figure 3:
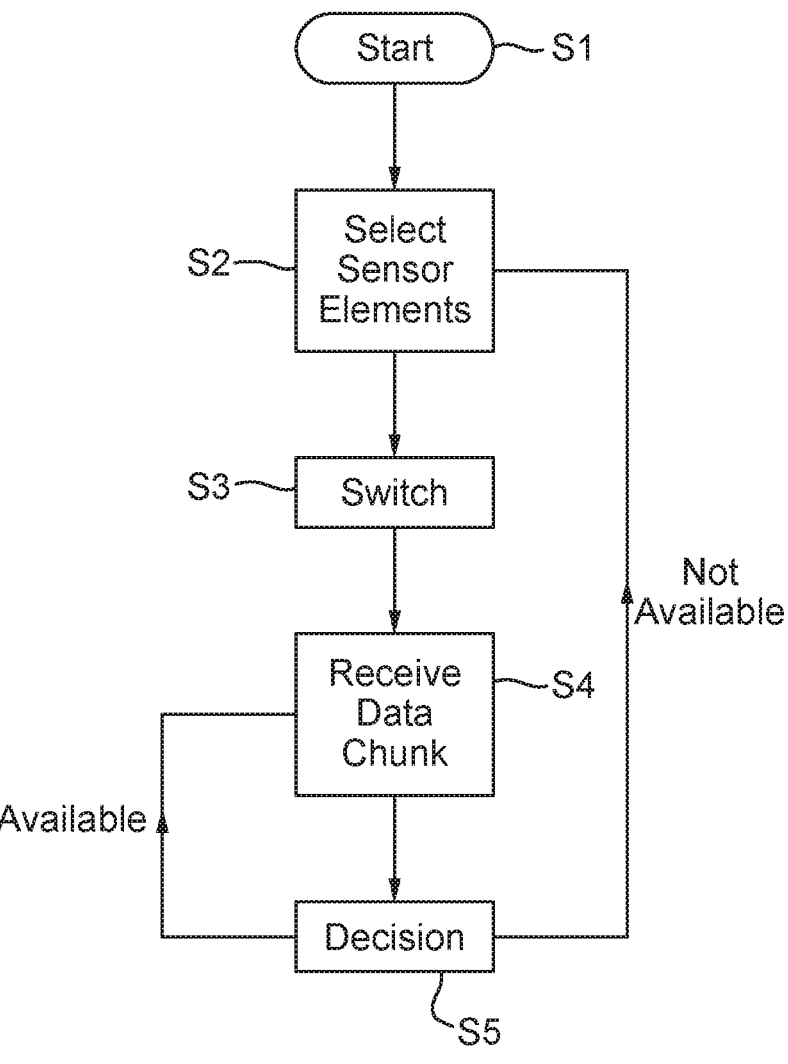
FIG. 3 is a flow chart of a method performed in a data processor of the biochemical sensing system.

Implementation of the control method shown in FIG. 3 improves the overall throughput of data collection from the sensor device 3 because the average waiting time between successive interactions may be significantly reduced, even under saturating concentrations of the molecular entities. This is because the probability of a molecular entity being available is greater at another sensor element 30 than at a sensor element 30 at which an interaction has just completed. Thus, on average the delay between completion of one interaction and collection of an electrical signal from a new interaction on the same detection channel 40 is reduced. This increased probability results from the availability of molecular entities to other sensor elements 30 due to the random processes in the sensor device 3.

To consider this another way, nanopores have interactions with nearby molecular entities faster than distant molecular entities. The occurrence of such interactions is probabilistic, limited by probability of molecular entities diffusing from the bulk of the sample into the vicinity of the nanopore. Typically, a nanopore sensing system captures and deplete molecular entities from the nearby vicinity faster than new molecular entities enter the that vicinity. In this case, the occurrence of interactions is limited by the rate at which new molecular entities enter the local vicinity from the bulk sample.

Similarly, sensitivity is increased, because a smaller amount of sample is required to saturate the sensing time. The amount of sample supplied to the sensing device 3 can be reduced without significantly impacting the sensing throughput, especially in the regime where the average time between interactions is less than the average interaction period.

This benefit is similar in both the first and second modes of operation of the bias control circuit 54.

In the first mode of operation, translocation may be occurring at any sensor element 30, so the switching increases the probability of the detection channel 40 receiving an electrical signal from a sensor element where that is happening. In this case, the likelihood is that a molecular entity will have partially translocated at the new sensor element 30 to which the detection channel 40 is connected. Thus, an electrical signal is obtained from parts of the molecular entity, i.e. the length of individual reads may be shorter, but the overall rate of data collection is nonetheless increased without significant detriment to the subsequent analysis. This may be appropriate in the cases of molecular entities that are fragments of a larger molecule, for example fragments of a polynucleotide, where the data is combined to estimate the identity of the entire molecular entity.

In the second mode of operation, translocation is inhibited until sensor elements 30 are connected to a detection channel 40. Accordingly, in this case, an electrical signal is obtained from the entire polymer in the case that the polymer translocates with respect to the nanopore. This may be appropriate in cases of molecular entities whose entire length needs to be analysed.

These benefits are particularly great in the case that the sensor elements 30 include means for capturing molecular entities in the vicinity of the nanopores, as described above, because this further increases the probability of other sensor elements 30 that are not connected to any detection channel 40 already having captured molecular entities while an electrical signal is captured from translocation at a sensor element 30 that is connected to a detection channel 40. With such capture a number of molecular entities can be retained in the vicinity of the nanopore without application of conditions that consume or deplete the molecular entities.

In the case of providing sensor elements 30 with capture moieties, even though the capture moieties are effective in capturing molecular entities, it may be difficult to load another molecular entity on a given sensor element 30 concurrently with sensing an interaction with a previously loaded molecular entity, for example even with use of a side-arm hybridisation. This could be due to steric or electrostatic exclusion effects from the molecular entity being sequenced preventing another molecular entity getting close enough to bind. In this case in particular, throughput and sensitivity may be achieved by stacking up the next molecular entity on an unused sensor element 30.

Figures 4A, 4B, 4C:
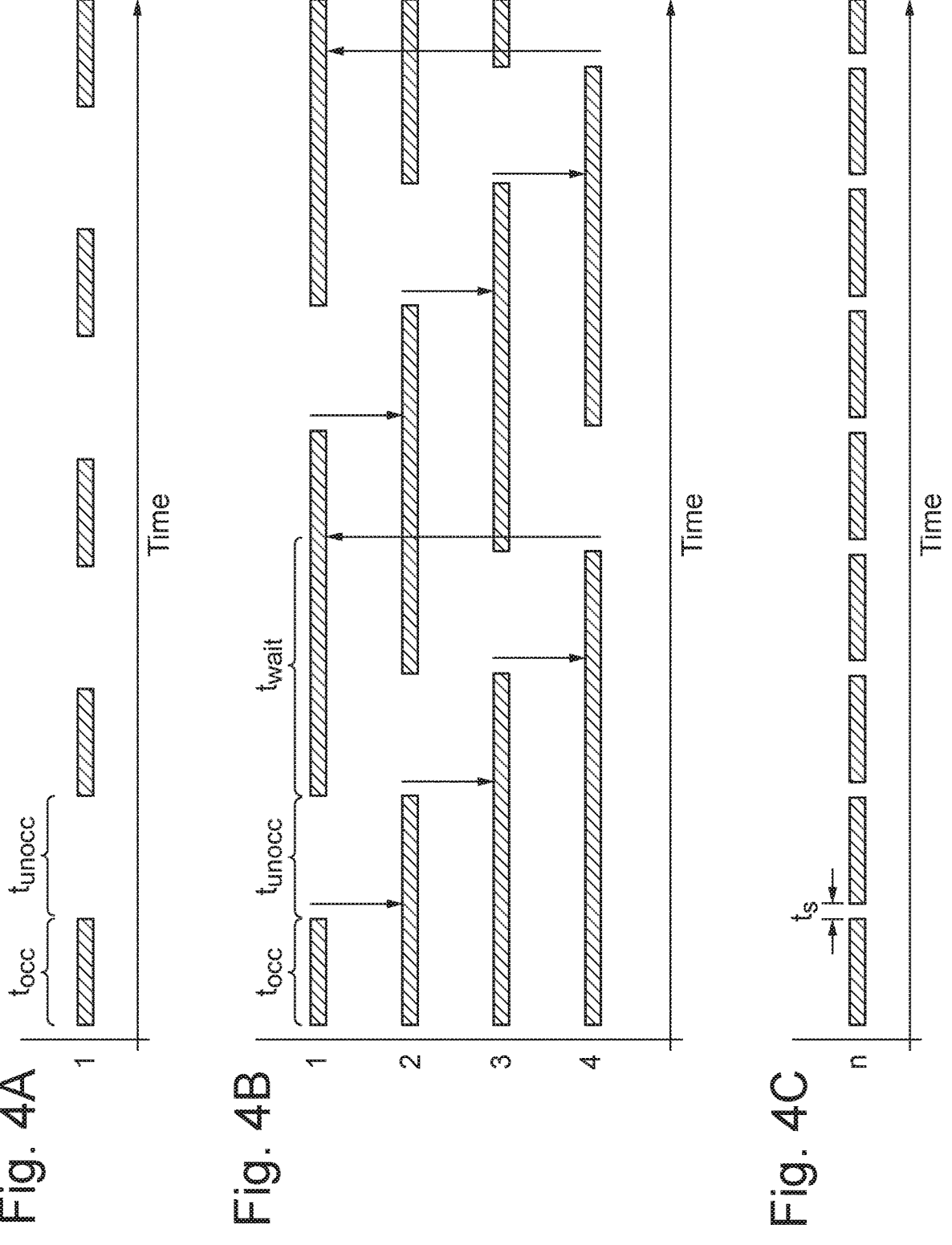
FIG. 4 is a set of three time schematics on the same timescale, time schematic (A) illustrating usage of a single sensor element in a comparative example, time schematic (B) illustrating usage of each of four sensor elements in an example of the present methods, and time schematic (C) shows overall usage of the a detection channel in that example.

FIG. 4 shows three time schematics (A) to (C) each on the same timescale for an example that illustrates the increased throughput provided by the present methods. The time schematics show occupied periods t-occ when a sensor element 30 has a molecular entity actively translocating with respect to its nanopore, unoccupied periods t-unocc when a sensor element 30 has no molecular entity actively translocating molecular entity actively translocating with respect to a nanopore, wait periods t-wait when a sensor element 30 has a molecular entity in the vicinity of the nanopore, but without translocation occurring, which could be achieved using the capture means described above, and switching periods t-s while the switching of the switch arrangement 30 occurs. Thus, this example corresponds to the second mode of operation of the bias control circuit 41, but similar advantage is achieved with the first mode of operation of the bias control circuit 41.

Time schematic (A) illustrates usage of a single nanopore without switching as a comparative example. After each occupied period t-occ when an interaction has completed, there is an unoccupied period t-unocc while waiting for a new interaction to occur. Thus, the throughput is reduced by the ratio between these periods.

Depending on the length of polymer being sensed, occupied period t-occ could be anywhere from 0.1 seconds through to 60+ minutes. The unoccupied period t-unocc depends on both analyte concentration and polymer length (for polymer analytes). The unoccupied period t-unocc increases with decreasing analyte concentration. The relationship is complicated by polymer length for polymer analytes, but, roughly speaking, longer polymers increase the unoccupied period t-unocc compared to shorter polymers, as the increased polynucleotide length makes it harder for the nanopore to see a free strand end.

Time schematic (B) illustrating usage of each of four sensor elements 30 when applying the present method switching cyclically between the four sensor elements 30, and time schematic (C) illustrates the overall usage of a detection channel connected to the four sensor elements in time schematic (B). As this is an example where the unoccupied period t-unocc is sufficiently short compared to the occupied period t-occ that when switching cyclically between the four sensor elements 30 it is always the case that a molecular entity is available for interaction at the new sensor element. Thus, the detection channel 40 always receives an electrical signal except during the switching periods t-s. Thus, throughput is greatly reduced as the switching periods t-s are shorter than the unoccupied period t-unocc. The switching period t-s is the time required by the detection circuit 5 itself, independent of the pore/analyte chemistry and can be up to ~1 sec.

The present methods are therefore particularly beneficial for both sensing long polymers (e.g. polynucleotides of at least 10, 20, 30, 40 or 50 kb in length), and/or for sensing at relatively low analyte concentration.

The invention claimed is:

1. A method of sensing interactions between molecular entities and nanopores, the method comprising:
    providing a sensor device comprising an array of sensor elements arranged to support respective nanopores that are capable of an interaction with a molecular entity and including respective electrodes, each sensor element being arranged to output an electrical signal at the electrode that is dependent on the interaction of the molecular entity with the nanopore;
    providing a detection circuit comprising:
        a plurality of detection channels each capable of amplifying the electrical signal from one of the sensor elements, the number of the sensor elements in the array being greater than the number of the detection channels; and
        a switch arrangement capable of selectively connecting the detection channels to the respective sensor elements;
    controlling the switch arrangement to connect the detection channels to the respective sensor elements; and
    detecting, on the basis of an analysis of the amplified electrical signal output from the detection channels, completion of the interactions at the sensor elements, and in response thereto, controlling the switch arrangement to connect the respective detection channel that is connected to the sensor element at which completion of the interaction has been detected to a new sensor element that is not currently connected to any of the detection channels.

2. The method according to claim 1, wherein the method further comprises, after the step of controlling the switch arrangement to connect the respective detection channel to the new sensor element that is not currently connected to any of the detection channels:
    determining, on the basis of an analysis of the amplified electrical signal output from the respective detection channel, whether the molecular entity is available for interaction at the new sensor element, and in response to determining that the molecular entity is available for interaction, continuing to connect the respective detection channel to the new sensor element, or in response to determining that the molecular entity is not available for interaction, controlling the switch arrangement to connect the respective detection channel to a further new sensor element that is not currently connected to any of the detection channels.

3. The method according to claim 1, wherein the molecular entities are polymers and the sensor elements are arranged to support the respective nanopores that are capable of interacting with the molecular entities during translocation of the molecular entities with respect to the respective nanopores.

4. The method according to claim 3, wherein the detection circuit further comprises a bias circuit arrangement capable of providing bias signals to the sensor elements that are capable of controlling the translocation of the molecular entities with respect to the nanopores of the respective sensor elements.

5. The method according to claim 4, wherein the method further comprises controlling the bias circuit arrangement to apply the bias signals arranged to cause the translocation of the molecular entities with respect to the nanopores of all the sensor elements.

6. The method according to claim 4, wherein the method further comprises causing the bias circuit arrangement to apply drive bias signals to the respective sensor elements when they are connected to one of the detection channels, wherein the drive bias signals are arranged to cause the translocation of the molecular entities with respect to the nanopores of the respective sensor elements, and to apply inhibition bias signals to the respective sensor elements when they are not connected to any of the detection channels, wherein the inhibition bias signals are arranged to inhibit translocation of the molecular entities with respect to the nanopores of the respective sensor elements.

7. The method according to claim 6, wherein the inhibition bias signals are selected to inhibit translocation of the molecular entities with respect to the nanopores of the respective sensor elements and to capture the molecular entities within a vicinity of the nanopores.

8. The method according to claim 3, wherein the molecular entities are double stranded deoxyribonucleic acid (DNA).

9. The method according to claim 8, the method further comprising providing an exonuclease on a cis side of the nanopores.

10. The method according to claim 1, wherein the sensor elements and/or the molecular entities are adapted to capture the molecular entities within a vicinity of the respective nanopores.

11. The method according to claim 10, wherein the sensor elements each comprise at least one capture moiety attached to the respective nanopore of the respective sensor element.

12. The method according to claim 1, wherein the sensor elements further comprise capture moieties arranged to capture the molecular entities within a vicinity of the respective nanopores.

13. The method according to claim 1, wherein the molecular entities are polynucleotides.

14. The method according to claim 1, wherein each nanopore is a protein pore.

15. The method according to claim 1, wherein each sensor element is arranged to support a membrane with the nanopore inserted in the membrane.

16. The method according to claim 1, wherein each nanopore is modified to comprise one or more binding sites for binding to one or more of the molecular entities.

17. The method according to claim 1, wherein each nanopore is a solid-state pore.

18. The method according to claim 1, wherein the electrical signal comprises ion current flowing through the respective nanopore.

19. The method according to claim 1, further comprising providing ionic solutions on either side of the nanopores.

\* \* \* \* \*